United States Patent [19]

Hoppe et al.

[11] 4,435,427

[45] Mar. 6, 1984

[54] STABLE INJECTABLE β-CAROTENE MICELLAR SOLUTIONS AND THEIR PREPARATION

[75] Inventors: Peter P. Hoppe, Wachenheim; Joachim U. Schneider, Weisenheim; Bernhard Schulz, Schwetzingen; Hubert Tiefenbacher, Leinfelden-Echterdingen, all of Fed. Rep. of Germany

[73] Assignee: BASF Aktiengesellschaft, Fed. Rep. of Germany

[21] Appl. No.: 329,124

[22] Filed: Dec. 9, 1981

[30] Foreign Application Priority Data

Dec. 19, 1980 [DE] Fed. Rep. of Germany ....... 3048000

[51] Int. Cl.$^3$ .......................................... A61K 31/015
[52] U.S. Cl. .................................................. 424/356
[58] Field of Search ................... 424/356, 173, 236, 59

[56] References Cited

U.S. PATENT DOCUMENTS 3,436,459  4/1969  Klaui ................................... 424/236
3,998,753  12/1976  Antoshkiw et al. ................. 252/312

FOREIGN PATENT DOCUMENTS 1210127  10/1964  Fed. Rep. of Germany ...... 424/294
2236899  2/1974  Fed. Rep. of Germany ...... 424/284
1041890  11/1963  United Kingdom ............... 424/237

*Primary Examiner*—Albert T. Meyers
*Assistant Examiner*—John W. Rollins
*Attorney, Agent, or Firm*—Keil & Witherspoon

[57] ABSTRACT

A process for the preparation of β-carotene micellar solutions, wherein a non-ionic emulsifier which is suitable for the preparation of micellar solutions is heated at from 160° to 180° C. and a total of from 20 to 30% by weight, based on the emulsifier, of β-carotene is introduced in the presence of a conventional antioxidant, the hot homogeneous mixture is cooled rapidly to below 100° C. by adding water, and the formulation is brought to the desired concentration of from 3 to 6% by weight by adding further water, and the β-carotene micellar solutions obtained by this process. The non-ionic emulsifiers used in this process have an HLB value of from 12 to 16, and are in particular oxyethylated triglycerides of fatty acids of 12 to 18 carbon atoms containing 20–60 oxyethylene units. Parenteral admininstration of the stable β-carotene micellar solutions according to the invention to cattle relieves the disturbed estrus cycle and impaired fertility caused by β-carotene deficiency.

10 Claims, No Drawings

STABLE INJECTABLE β-CAROTENE MICELLAR SOLUTIONS AND THEIR PREPARATION

The present invention relates to stable injectable micellar solutions of β-carotene and a process for their preparation.

β-Carotene has the chemical formula:

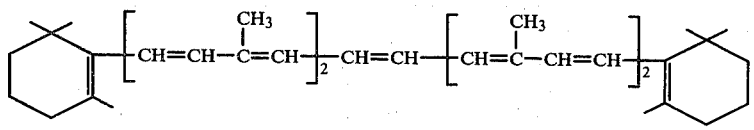

Studies by Lotthammer (cf. Dtsch. Tierärtzl. Wschr. 82 (1975), 444–49; 83 (1976), 353–58; 84 (1977), 220–26 and 307–310; and 85, (1978), 7–12) have shown that β-carotene deficiency in cattle causes a disturbed estrus cycle and poor fertility. A low β-carotene blood level charactrerizes the deficiency.

β-Carotene dificiency has hitherto been treated by feeding animals with carotene-rich straight fodder, such as lucerne green meal, grass green meal or carrots, and/or dry synthetic β-carotene powder. However, oral administration of β-carotene has little effect on its level in blood, because absorption of βcarotene from the intestinal tract is poor.

In contrast, the blood level can be increased rapidly and over a relatively long period by parenteral administration of β-carotene.

For such administration, the formulations to be injected should have a relatively high content of β-carotene in extremely finely divided form, so that the volume to be injected is kept to a minimum.

In the case of animals which have a relatively low level of β-carotene in the blood plasma, it is not possible to increase this level rapidly (within two days) and ecohomically by a gastroenteral route, so that the β-carotene must be administered parenterally.

However, conventional solutions of β-carotene in vegetable oils contain not more than 0.3–0.5% (Ullmanns Enzyklopädie der technischen Chemie, Volume 11 (1976), page 106), and such concentrations are too low if the required dose of 500 mg of β-carotene is to be administered in the usual injection volume of 10–20 ml.

Japanese Preliminary Published Application No. 38,556/1970 discloses that carotenoid compounds can be converted into water-soluble carotenoid preparations by dissolving them together with aliphatic esters of sugars, heating the solution and removing the solvent. However, the solutions of β-carotene which can be prepared in this manner are of only about 0.2% strength.

German Published Application DAS No. 1,210,127 discloses carotene emulsions containing polyoxyethylated castor oil or polyoxyethylene sorbitan fatty acid esters as emulsifiers, together with ionic wetting agents. However, these emulsions are not stable for a prolonged period, since the carotene crystallizes out.

German Laid-Open Application DOS No. 2,236,899 therefore proposes the preparation of more highly concentrated emulsions using special soaps, namely soaps of tris-(hydroxymethyl)-aminomethane and saturated or unsaturated fatty acids of 9 to 20 carbon atoms. However, the method proposed in that Application is not satisfactory, since on the one hand the procedure presents difficulties in practice, and on the other hand only water-miscible carotenoid emulsions containing not more than 4% of β-carotene can be prepared.

It is an object of the present invention to prepare relatively highly concentrated clear stable emulsions or micellar solutions of β-carotene.

We have found that this object is achieved by a process for the preparation of β-carotene miscellar solutions wherein a non-ionic emulsifier which is suitable for the preparation of micellar solutions is heated at from 160° to 180° C. and a total of from 20 to 30% by weight, based on the emulsifier, of β-carotene is introduced in the presence of a conventional antioxidant, the hot homogeneous mixture is cooled rapidly to below 100° C. by adding water, and the formulation is brought to the desired concentration of from 3 to 6% by weight by adding further water, and by the stable injectable β-carotene micellar solutions obtainable by this process.

It is surprising that not just a milky turbid β-carotene emulsion but a transparent β-carotene micellar solution containing up to 6% by weight of β-carotene can be obtained in the manner described.

Non-ionic emulsifiers which are suitable for the preparation of micellar solutions are those having an HLB value (cf. H. P. Fiedler, Lexikon der Pharmazie, Kosmetik und angrenzenden Gebiete, 1971, pages 263–270, especially pages 267–69) of from 12 to 16, especially oxyethylated triglycerides of fatty acids of 12 to 18 carbon atoms containing 20–60 oxyethylene units, oxyethylated sorbitan fatty acid esters having about 20 oxyethylene units, or oxyethylated monohydroxy-fatty acids having from 14 to 17 oxyethylene units, such as are disclosed in German Laid-Open Application DOS No. 2,911,241. Such emulsifiers are also called solubilizers, because they are soluble in water and thereby act as solubilizing agents for lipophilic substances by keeping these in micellar solution. Micellar solutions are transparent and clear.

Examples of particularly suitable non-ionic emulsifiers are: glyceryl polyoxyethylene glycol ricinoleate, glycerol polyoxyethylene glycol hydroxystearate, polyoxyethylene-20 sorbitan mono-oleate, polyoxyethylene-20 sorbitan monostearate and the adduct monohydroxystearic acid with 15 units of ethylene oxide.

Specifically, the micellar solutions are prepared by adding from 20 to 30% by weight, based on the emulsifier, of β-carotene a little at a time to the emulsifier, which is heated at from 160° to 180° C. and contains conventional antioxidants, whereupon the βcarotene melts and dissolves virtually immediately. The mixture is rapidly brought to below 100° C. by adding water, and the formulation is then brought to the desired concentration by adding further water. After filtration and cooling to room temperature, a stable 4–6% preferably about 5%, strength by weight transparent micelllar solution is obtained, which is still stable after 12 months.

Examples of conventional antioxidants which can be used in the process according to the invention are butylhydroxytoluene, butylhydroxyanisole and d,l-α-tocopherol. The antioxidants are generally used in amounts of from 10 to 20% by weight, based on the β-carotene employed.

According to the examples in German Laid-Open Application DOS. No. 2,236,899, temperatures above 110° C. are to be avoided when the β-carotene is introduced into the emulsifier. This requirement is understandable to those skilled in the art, since at higher temperatures isomerization of β-carotene is to be feared.

It is therefore surprising that the procedure according to the invention gives a micellar solution which is sufficiently concentrated for injection purposes and which displays its full action in animals even though some of the β-carotene has probably been isomerized.

EXAMPLE 300 g of Chromophor EL ® (glycerolpolyoxyethyleneglycol ricinoleate) and 6 g of butylhydroxytoluene are introduced into a 2 1 4-necked round-bottomed flask fitted with a stirrer, nitrogen inlet and reflux condenser. The mixture is heated to an internal temperature of 160° C., whilst being stirred and gassed with nitrogen. 66 g of β-carotene are added in the course of about 5 minutes. The heating bath is removed and water is added dropwise until the internal temperature of the mixture has fallen to 100° C. The mixture is brought to 60°-80° C. by rapid addition of the remainder of the water (total amount: 828 g) and by using the heating bath. The still warm micellar solution is filtered through a glass filter frit to give an about 5% strength transparent β-carotene solution which can be used as an injection solution.

ANIMAL EXPERIMENTS 3 experimental groups (Friesian heifers) were compared. They were treated as follows:

Group 1 received 10 ml of an aqueous β-carotene micellar solution according to the invention, containing 450 mg of β-carotene, intramuscularly.

Group 2 received an intramuscular injection of an oily β-carotene solution containing 450 mg of β-carotene.

Group 3 received no β-carotene injection.

The average plasma levels of β-carotene (μg/100 ml) in the test animals were measured before the treatment and 1, 2, 4 and 32 days after the treatment.

| Group | Average plasma β-carotene level (μg/100 ml) | | | | |
| --- | --- | --- | --- | --- | --- |
|  | Day 0 | Day 1 | Day 2 | Day 4 | Day 32 |
| 1 | 230 | 1,547 | 1,705 | 1,214 | 369 |
| 2 | 221 | 288 | 371 | 355 | 232 |
| 3 | 182 | 183 | 191 | 204 | 207 |

As can be seen from the experiment, when the aqueous β-carotene injection preparation was administered, the blood level was at all times significantly higher than when the comparative product was administered. It is thus possible to eliminate β-carotene deficiency for more than 1 month with a single injection and to ensure a physiological estrus cycle.

We claim:

1. A process for the preparation of a β-carotene micellar solution, which comprises: forming a melt having a temperature of from 160° to 180° C. of a mixture of β-carotene, an antioxidant for β-carotene and a non-ionic and water-soluble emulsifier having an HLB value of from 12 to 16 and which is capable of forming a homogeneous melt with said β-carotene, the amount of β-carotene in the melt being from 20 to 30% by weight, based on the weight of the emulsifier;

adding water to the mixture to cool the melt rapidly to a temperature below 100° C.; and thereafter, adding additional water to the chilled mixture to form a clear micellar solution having a concentration of β-carotene of from 3 to 6% by weight.

2. The process of claim 1, wherein an oxyethylated triglyceride of a fatty acid of 12 to 18 carbon atoms containing 20-60 oxyethylene units is used as the non-ionic emulsifier.

3. The process of claim 1, wherein glycerol polyoxyethylene glycolrincinoleate is used as the non-ionic emulsifier.

4. The process of claim 1, wherein polyoxyethylene glycerol polyoxyethylene glycolhydroxystearate is used as the non-ionic emulsifier.

5. The process of claim 1, wherein a polyoxyethylated sorbitan fatty acid ester is used as the non-ionic emulsifier.

6. The process of claim 1, wherein polyoxyethylene-20 sorbitan monooleate is used as the non-ionic emulsifier.

7. The process of claim 1, wherein polyoxyethylene-20 sorbitan monostearate is used as the non-ionic emulsifier.

8. The process of claim 1, wherein the adduct of monohydroxystearic acid with 15 units of ethylene oxide is used as the non-ionic emulsifier.

9. The process of claim 1, wherein from 10 to 20% by weight, based on the β-carotene, of butylhydroxytoluene, butylhydroxyanisole or d,l-β-tocopherol is used as the antioxidant.

10. A stable aqueous injection solution which contains from 3 to 6% by weight of β-carotene and is obtained by introducing into a, water soluble emulsifier, which is suitable for the preparation of a micellar solution and is heated at from 160° to 180° C. a total of from 20 to 30% by weight, based on the emulsifier, of β-carotene, rapidly cooling the resulting hot homogeneous mixture to below 100° C. by adding water and bringing the formulation to the desired final concentration of from 3 to 6% by weight of β-carotene by adding further water.

* * * * *

UNITED STATES PATENT AND TRADEMARK OFFICE
CERTIFICATE OF CORRECTION

PATENT NO. : 4,435,427
DATED : March 6, 1984
INVENTOR(S) : Peter HOPPE et al.

It is certified that error appears in the above-identified patent and that said Letters Patent is hereby corrected as shown below:

IN THE CLAIMS:

Claim 4, line 1, cancel "polyoxyethylene".

Claim 9, line 3, correct "d,1-β-tocopherol" to read "d,1-α-tocopherol".

Claim 10, line 3, after "a" insert "non-ionic".

Signed and Sealed this

Twenty-ninth Day of May 1984

[SEAL]

Attest:

GERALD J. MOSSINGHOFF

Attesting Officer

Commissioner of Patents and Trademarks